US012646818B2

(12) United States Patent
Schwarz et al.

(10) Patent No.: US 12,646,818 B2
(45) Date of Patent: Jun. 2, 2026

(54) WIRELESS COMMUNICATION MODULE FOR MEDICAL FLUID PUMP

(71) Applicant: B. Braun Melsungen AG, Melsungen (DE)

(72) Inventors: Jan Schwarz, Melsungen (DE); Christoph Erlen, Kassel (DE); Carsten Niemeier, Kassel (DE); Marcel Stich, Nieste (DE); Michael Kauba, Fuldabrueck (DE); Michael Ostermoeller, Bad Hersfeld (DE)

(73) Assignee: B. Braun Melsungen AG, Melsungen (DE)

( * ) Notice: Subject to any disclaimer, the term of this patent is extended or adjusted under 35 U.S.C. 154(b) by 853 days.

(21) Appl. No.: 17/968,053

(22) Filed: Oct. 18, 2022

(65) Prior Publication Data

US 2023/0120949 A1    Apr. 20, 2023

(30) Foreign Application Priority Data

Oct. 19, 2021    (DE) ...................... 10 2021 127 113.4

(51) Int. Cl.
| | |
|---|---|
| *A61M 5/142* | (2006.01) |
| *H01Q 1/22* | (2006.01) |
| *H01Q 1/52* | (2006.01) |
| *H01Q 21/06* | (2006.01) |

(52) U.S. Cl.
CPC .............. *H01Q 1/22* (2013.01); *A61M 5/142* (2013.01); *H01Q 1/526* (2013.01); *H01Q 21/06* (2013.01)

(58) Field of Classification Search
CPC ..................... A61M 2205/3546; A61M 5/142; H01Q 1/22; H01Q 1/526; H01Q 1/52; H01Q 21/06

USPC .......................................... 343/702; 361/748
See application file for complete search history.

(56) References Cited

U.S. PATENT DOCUMENTS

| | | | |
|---|---|---|---|
| 6,388,879 | B1 | 5/2002 | Otaguro et al. |
| 8,213,872 | B2 | 7/2012 | Lambrecht |
| 8,965,287 | B2 | 2/2015 | Lam |
| 2003/0050555 | A1 | 3/2003 | Critchlow et al. |
| 2004/0185897 | A1 | 9/2004 | Ostervall |

(Continued)

FOREIGN PATENT DOCUMENTS

| | | |
|---|---|---|
| DE | 202021103518 U1 | 8/2021 |
| KR | 102278616 B1 | 7/2021 |

OTHER PUBLICATIONS

Search Report received in German Application No. 10 2021 127 113.4 dated Sep. 16, 2022, with translation, 11 pages.

(Continued)

*Primary Examiner* — Timothy J Thompson
*Assistant Examiner* — Guillermo J Egoavil
(74) *Attorney, Agent, or Firm* — CM Law; Christopher A. Rothe

(57) ABSTRACT

A medical fluid pump, such as an infusion pump or syringe pump, includes a printed circuit board equipped with control devices of the medical fluid pump. The control device can include at least the control device of a motor of the medical fluid pump. The medical fluid pump also includes a wireless communication module in the form of a communication circuit board. The communication circuit board is arranged substantially perpendicular or orthogonally to the printed circuit board.

14 Claims, 2 Drawing Sheets

(56)            References Cited

U.S. PATENT DOCUMENTS

2013/0329352 A1 *  12/2013  Nigen ....................... G06F 1/20
                                                  361/708
2015/0123854 A1 *   5/2015  Chakam ............... H01Q 1/1214
                                                  343/702
2020/0203834 A1     6/2020  Asaf et al.
2021/0170097 A1 *   6/2021  Kamen ............. A61M 5/16886

OTHER PUBLICATIONS

Search Report received in European Application No. 22201669.3-1122 dated Mar. 3, 2023, with translation, 12 pages.
Office Action received in European Application No. 22 201 669.3-1122 dated Jan. 28, 2026, with translation, 9 pages.

* cited by examiner

WIRELESS COMMUNICATION MODULE FOR MEDICAL FLUID PUMP

CROSS-REFERENCE TO RELATED APPLICATION

This application claims priority under 35 U.S.C. § 119 to German Patent Application No. 10 2021 127 113.4, filed Oct. 19, 2021, the content of which is incorporated by reference herein in its entirety.

FIELD

The present disclosure relates to a medical fluid pump, in particular in the form of an infusion pump or syringe pump, having a wireless communication module in the form of a communication circuit board.

BACKGROUND

In medicine, fluid pumps, in particular syringe pumps and infusion pumps or peristaltic pumps, are widely used to supply a patient with a defined dose of medication.

Such medical fluid pumps have been equipped with more and more smart functions in recent years. These smart functions are implemented via additional printed circuit boards or chips, which are mostly configured as additionally purchased parts. These additional printed circuit boards or chips are provided and configured to be mounted on the surface of a motherboard or a mainboard. As a result, the motherboard has to be larger than in the case where no smart functions are configured in the medical fluid pump. Such an enlarged motherboard requires a larger footprint, which results in the medical fluid pump increasing in size and thus taking up more space. This makes it more difficult for medical personnel to access a patient who is being supplied with the medical fluid pump.

In order to get around this problem, it was considered to implement the smart functions directly on the motherboard. This would reduce the increase in space requirements. However, this would make the motherboard considerably more expensive, and if individual smart functions fail, the expensive motherboard would need to be replaced directly.

Furthermore, it was discussed to limit the number of smart functions to counteract the increase in installation space. However, this would result in the abandonment of various smart functions.

SUMMARY

Accordingly, the object and aim of the present invention are to provide a medical fluid pump that is equipped with smart functions without taking up more space and without having the disadvantages discussed above.

The medical fluid pump, preferably in the form of an infusion pump or syringe pump, comprises a printed circuit board equipped with the substantial control devices of the medical fluid pump, namely at least the control device of a motor of the medical fluid pump, and a wireless communication module in the form of a communication circuit board. The communication circuit board is arranged substantially perpendicular or orthogonal to the printed circuit board, respectively.

In other words, the medical fluid pump has a printed circuit board, which can also be referred to as a main board or motherboard. On this printed circuit board, the control devices essential for the function of the medical fluid pump are implemented. The essential control devices for the function of the medical fluid pump include at least the control device of the motor of the fluid pump, which is responsible for the application of the fluid or the drug. Preferably, in addition to the control device for the motor of the fluid pump, monitoring of the motor on the fluid pump may also be implemented on the printed circuit board. Additionally, in a set of smart circuit boards implementing smart functions, the medical fluid pump includes the wireless communication module in the form of the communication circuit board. The communication circuit board includes various devices that enable wireless communication of data, preferably via WLAN and/or Bluetooth and/or any wireless radio technology, between the medical fluid pump and an external device. The communication circuit board is arranged in its planar extent substantially perpendicular or orthogonal to the planar extent of the printed circuit board. In yet other words, the angle between the planar extent of the communication circuit board and the planar extent of the printed circuit board is between 80° and 100°, preferably between 85° and 95°, and in particular preferably 90°.

It has become apparent to the Applicant that in particular the communication circuit board is one of the smart circuit boards necessary for the smart functions, which requires a considerable amount of space. By selecting the communication circuit board from a set of printed circuit boards implementing smart functions and arranging the communication circuit board perpendicularly or orthogonally to the printed circuit board, the footprint of the communication circuit board projected onto the printed circuit board is considerably reduced and the printed circuit board can be made more compact than in the case where the communication circuit board is oriented flat/parallel to the printed circuit board. This can ensure that the dimensions of the medical fluid pump do not change from the case where no wireless communication module is provided in the medical fluid pump. Furthermore, by orienting the communication circuit board orthogonally to the printed circuit board, air can circulate around the communication circuit board better than in the case of planar/parallel orientation. This improves the cooling of the communication circuit board. Such an orientation of the communication circuit board is in direct contrast to the usual orientation of the communication circuit board.

In a first aspect, the communication circuit board may be enclosed or surrounded by a (shield) cage that is metallic or contains metallic elements.

In other words, the communication circuit board is enclosed by metallic sheets or a metallic grid cage or a plastic cage containing metallic elements, for example in the form of metallic particles.

In yet other words, the communication circuit board is shielded in particular against high-frequency electromagnetic fields with the aid of metallic elements. In addition, interference radiation emanating from the communication circuit board is also shielded. By shielding the communication circuit board against electromagnetic radiation/fields, it can be ensured that the function of the communication circuit board is not impaired by electromagnetic radiation from the environment. In other words, the cage ensures optimized EMC/ESD stability.

In a further aspect, the cage may be connected to the communication circuit board at individual, spaced-apart points, in particular at four points.

In other words, the cage is connected to the communication circuit board at four connection points, preferably located at the four corners of the communication circuit board.

In a further aspect, the cage may be firmly bonded, in particular by soldering, to the communication circuit board at two points and may be force-fitted, in particular by clamping, to the communication circuit board at two points.

In other words, the cage is firmly bonded to the communication circuit board at two connection points located on the same edge of the communication circuit board. The cage is force-fitted to the communication circuit board at two further connection points of the communication circuit board, which are located at a further edge of the communication circuit board.

The connection via force-fit enables a displacement of the force-fitted connection points in the event of forces occurring between the cage and the communication circuit board when the occurring force exceeds a certain threshold value. This ensures that in the event of a possible expansion of the metallic cage, for example due to an increase in temperature, no excessively large stresses are transferred into the communication circuit board which could damage the communication circuit board.

In a further aspect, the cage may be connected to a ground potential of the printed circuit board.

In other words, the cage is connected in an electrically conducting manner to the ground (GND) of the printed circuit board.

In a further aspect, the communication circuit board may be connected to several, in particular two, antennas.

In other words, more than one antenna is provided that is connected to the communication circuit board. Preferably, there are two antennas, wherein the antennas are configured separately from the communication circuit board.

In yet other words, the communication circuit board has MIMO (multiple input multiple output) interfaces. This enables coding methods that use not only a temporal dimension but also a spatial dimension for information transmission. This allows both the quality in terms of bit error frequency and the data rate of the wireless connection to be significantly improved.

By providing the antenna and communication circuit board separately, it is further possible to arrange the antennas at positions suitable for transmission performance.

In a further aspect, the several, in particular two, antennas may be arranged orthogonally to each other.

In other words, the spatial orientation of the antennas differs from each other by essentially 90°. The transmission power can be increased by the orthogonal directionality of the antennas. In particular, a coverage area can be increased by the radiation pattern of the antennas due to the orthogonal arrangement.

In a further aspect, the several, in particular two, antennas may be connected to the communication circuit board via cables, wherein the cable lengths of the cables connecting the communication circuit board to the antennas are identical.

In other words, identically constructed cables are used to connect the antennas to the communication circuit board. The preferred cable length is 175 mm. On the one hand, this reduces the number of spare parts and simplifies assembling of the medical fluid pump. On the other hand, the identical cable length ensures that there are no runtime differences between the antennas and the communication circuit board. The cables are laid on the printed circuit board via clips. The cable and thus the antennas are connected to the ground potential (ground) of the printed circuit board via the clips.

In a further aspect, the antennas may be arranged at a distance from each other corresponding to a multiple of a quarter, in particular a multiple of a half, wavelength of the transmission frequency of the antenna.

In other words, the transmission frequency of the antennas is 2.4 GHz and/or 5 GHz. The wavelength is 12.5 cm for 2.4 GHz and 6 cm for 5 GHz. The distance between the antennas is thus a multiple of 3.125 cm or a multiple of 3 cm, respectively. By arranging the antennas in this way, interference between the antennas is minimized.

In a further aspect, the communication circuit board is thermally coupled to the printed circuit board.

In other words, the communication circuit board is connected to the printed circuit board via a thermally conductive component. Due to the high metal content of the printed circuit board and the large surface area of the printed circuit board, the printed circuit board acts as a heat sink for the communication circuit board and prevents the communication circuit board from overheating.

In a further aspect, the communication circuit board may operate independently of the printed circuit board.

In other words, the printed circuit board and the communication circuit board exchange data packets, wherein both the printed circuit board and the communication circuit board function independently of each other. This ensures that in the event of a failure or temporary malfunction of the communication circuit board, the essential functions of the medical fluid pump controlled by the printed circuit board can continue to be performed.

In a further aspect, the substantial functions of the medical fluid pump can be controlled wirelessly via the communication circuit board. In particular, a medication application can be started, paused, or stopped.

In a further aspect, the communication circuit board may wirelessly communicate information about malfunctions in the function of the printed circuit board to, for example, a practitioner and/or the manufacturer of the fluid pump.

In a further aspect, a software update for the medical fluid pump and/or the drug database stored on the medical fluid pump can be wirelessly transmitted to the medical fluid pump via the communication circuit board.

DETAILED DESCRIPTION

Figures 1, 2:
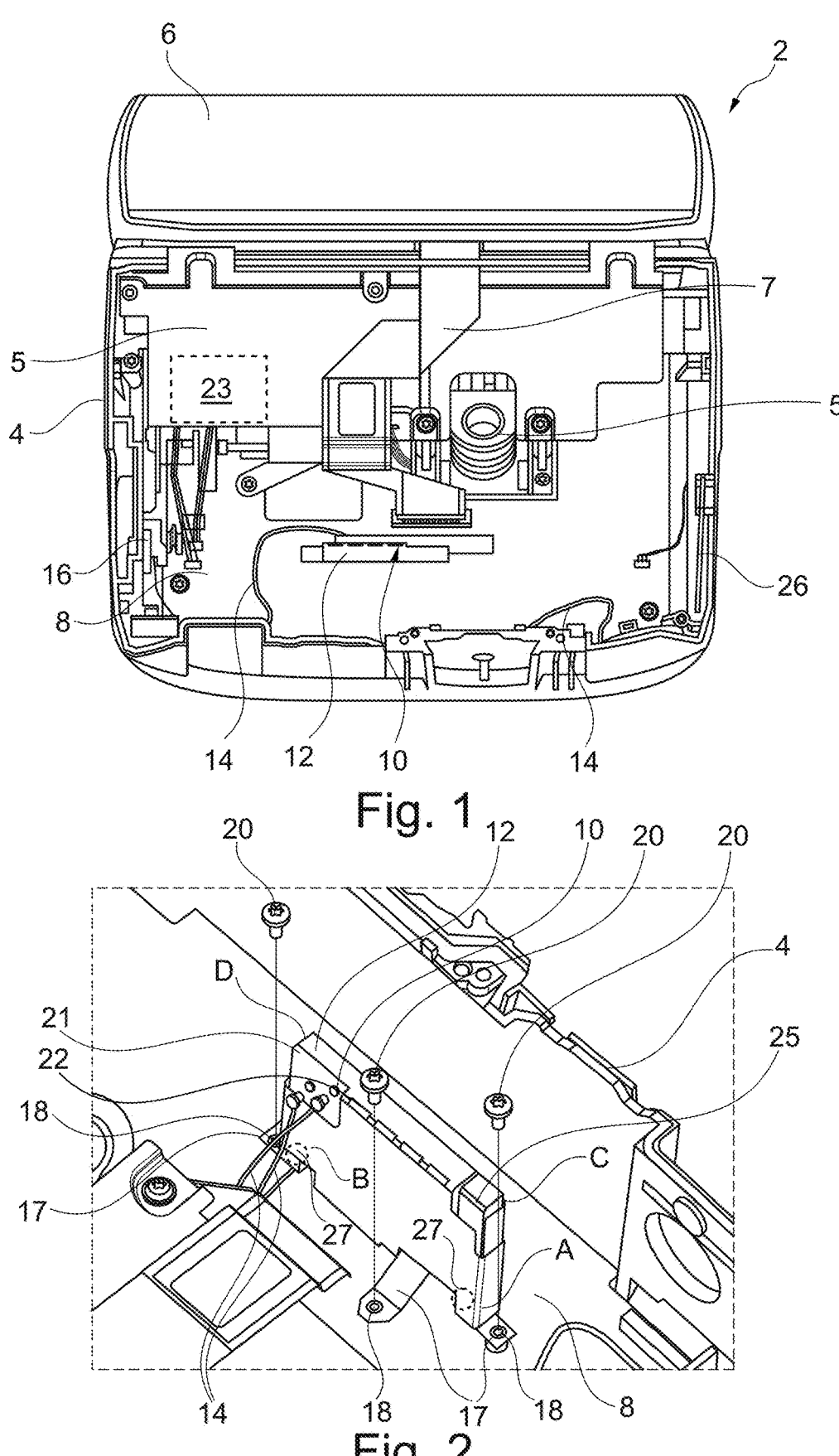
FIG. 1 is an interior view of a medical fluid pump according to the invention.
FIG. 2 is an enlarged representation of a section of the interior view of the medical fluid pump according to the invention with a wireless communication module in the form of a communication circuit board.

FIG. 1 shows an internal view of a medical fluid pump 2 according to the invention, comprising a substantially rectangular housing 4, drive components 5, and a front flap 6 attached to a front side of the housing 4 of the medical fluid pump 2, which is connected via a connecting cable 7. The medical fluid pump 2 includes in the housing 4, a printed circuit board/main board 8, which is equipped with the substantial control devices of the medical fluid pump 2, namely at least with the control device of a motor 23 (shown schematically) of the medical fluid pump 2, and a wireless communication module in the form of a communication circuit board 10. The communication circuit board 10 is arranged substantially perpendicularly or orthogonally to the printed circuit board 8. In other words, a narrow side of the communication circuit board 10 contacts the surface of the printed circuit board 8. The communication circuit board 10 is arranged substantially centrally with respect to a width direction of the housing 4. The communication circuit board 10 is enclosed by a metallic shield cage 12. The communication circuit board 10 is connected to antennas 16, 26 via cables 14. The antennas 16, 26 are each arranged on side walls of the housing 4 of the medical fluid pump 2. A distance between the antennas 16, 26 to each other is a multiple of a quarter or a half wavelength of the transmission frequency of the antennas 16, 26.

FIG. 2 shows the communication circuit board 10 in the shield cage 12 on the printed circuit board 8. The shield cage 12 encloses the communication circuit board 10 from six sides and prevents electromagnetic fields or radiation from influencing or interfering with the function of the communication circuit board 10. The shield cage 12 is made of sheet metal. The shield cage 12 has three feet 17, each of which is provided with a clearance hole 18. The shield cage 12 is connected to the printed circuit board 8 through the clearance holes 18 via screws 20. By providing three feet 17, the shield cage 12 is fixed in a statically determined manner. The shield cage 12 has a first port opening (not shown) on the side facing the printed circuit board 8. Through the first port opening, the communication circuit board 10 is connected to the printed circuit board 8 via a printed circuit board connector. Furthermore, the shield cage 12 has a second port opening 21 in a side surface of the shield cage 12 oriented orthogonally to the printed circuit board 8. Through the second port opening 21, the cables 14 connecting the communication circuit board 10 to the antennas 16 are connected to the communication circuit board 10. The shield cage 12 furthermore includes ventilation slits 22 that improve an air exchange between an interior of the shield cage 12 and an interior space of the housing 4 of the medical fluid pump, such that a buildup of warm air in the shield cage 12 is prevented. In two corner portions of the shielding cage 12 facing away from the printed circuit board 8 in an assembled state, clamping elements 25 are configured, which connect the shielding cage 12 to the communication circuit board 10 in a force-fit manner at a third point C and a fourth point D. In two corner sections of the shielding cage 12 facing the printed circuit board 8 in an assembled state, the shielding cage 12 is connected to the communication circuit board 10 in a firmly bonded manner at a first point A and a second point B. The shielding cage 12 may be firmly bonded to the first point A and the second point B by soldering 27, as schematically shown in FIG. 2.

Figure 3:
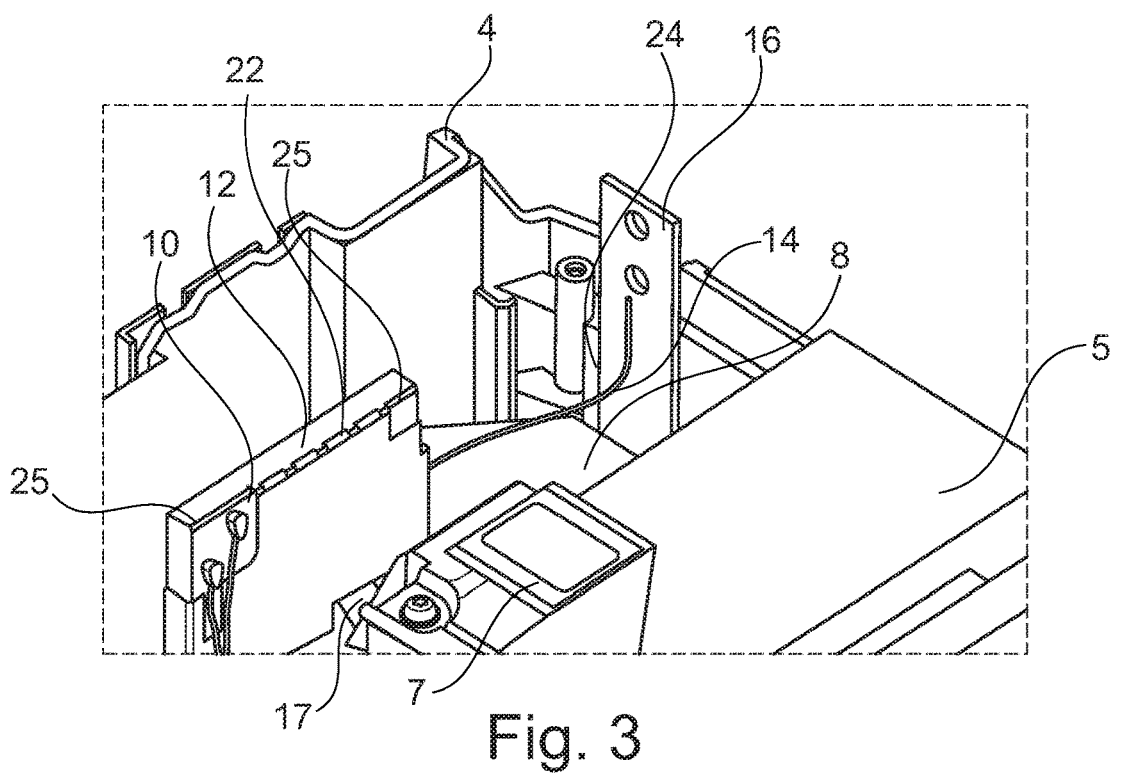
FIG. 3 is a further enlarged representation of a section of the interior view of the medical fluid pump according to the invention with the wireless communication module in the form of the communication circuit board and a first antenna.

FIG. 3 shows the communication circuit board 10 in the shield cage 12 on the printed circuit board 8 and a first antenna 16 connected via cable 14. The first antenna 16 is oriented orthogonally to the printed circuit board 8 and is attached to an inner side of the side wall of the housing 4 of the medical fluid pump 2. A vertical antenna receptacle 24 is configured in the housing 4 to receive the first antenna 16, and the vertical antenna receptacle 24 receives the antenna 16 in a form-fitting manner. The vertical antenna receptacle 24 is formed by two rails extending in a direction orthogonal to the printed circuit board 8. The rails are configured integrally with the housing 4.

Figure 4:
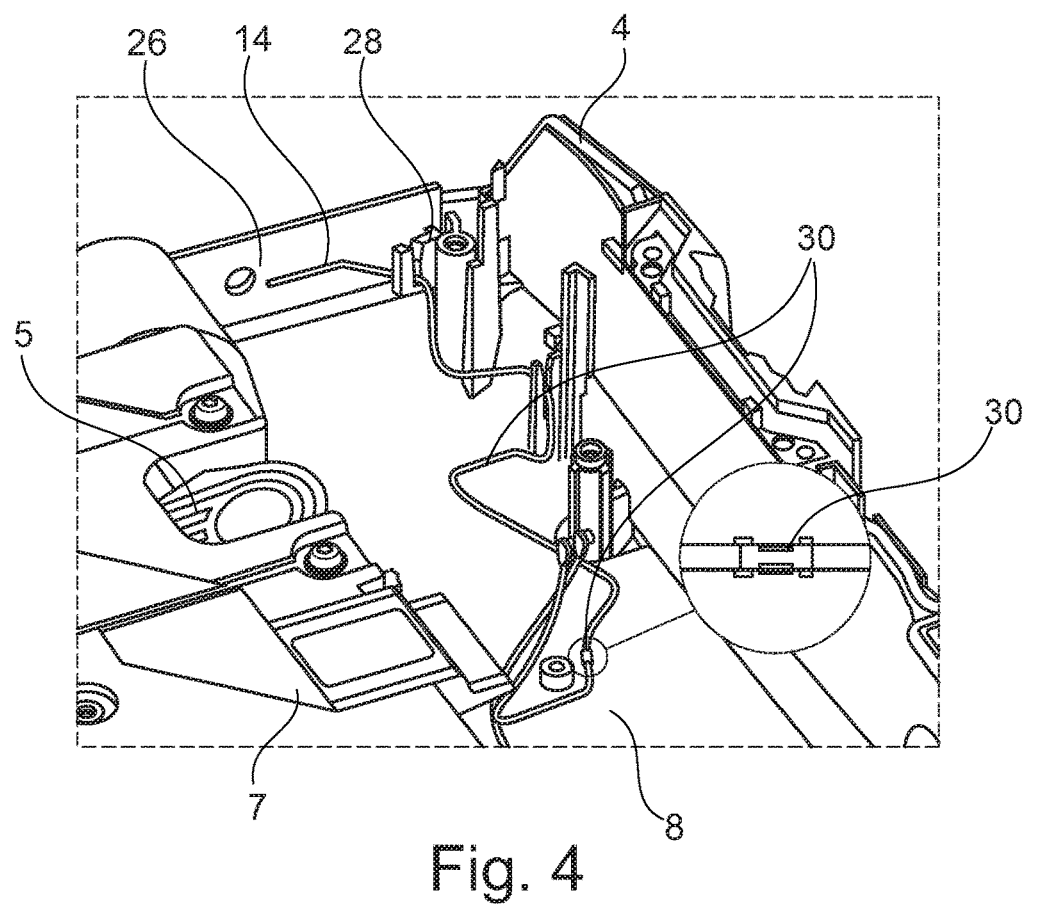
FIG. 4 is another enlarged view of a section of the interior view of the medical fluid pump according to the invention with a second antenna.

FIG. 4 shows a further section of the interior of the housing 4 of the medical fluid pump with the printed circuit board 8, the cables 14 and a second antenna 26, wherein the communication circuit board 10 has been omitted for clarity. The second antenna 26 is oriented parallel to the printed circuit board 8 and is thus oriented 90° out of orientation with respect to the first antenna 16. The second antenna 26 is attached to an inner side of the side wall of the housing 4 of the medical fluid pump, which is opposite the first antenna. A horizontal antenna receptacle 28 is configured in the housing 4 to receive the second antenna 26, which receives the antenna 26 in a form-fitting manner. The horizontal antenna receptacle 28 is formed by two rails extending in a direction orthogonal to the printed circuit board 8. The rails are configured integrally with the housing 4. Both the first antenna 16 and the second antenna 26 are connected to the communication circuit board 10 via the cables 14. The cable 14 between the communication circuit board 10 and the first antenna 16, and the cable 14 between the communication circuit board and the second antenna 26 have identical lengths. The cables 14 are fixed to the printed circuit board 8 via cable clips 30. Via the cable clips 30, the antennas 16, 26 are connected to a ground potential of the printed circuit board 8.

What is claimed:

1. A medical fluid pump comprising:
a motor;
a printed circuit board having a control device of the motor; and
a wireless communication module comprising a communication circuit board,
the communication circuit board being arranged substantially perpendicular to the printed circuit board,
wherein:
wherein the communication circuit board is enclosed by a cage that is metallic or contains metallic elements, and
the cage is connected to a ground potential of the printed circuit board.

2. The medical fluid pump according to claim 1, wherein the cage is connected to the communication circuit board at individual, spaced-apart points.

3. The medical fluid pump according to claim 1, wherein the cage is firmly bonded to the communication circuit board at a first point and a second point, and wherein the cage is force-fitted to the communication circuit board at a third point and a fourth point.

4. The medical fluid pump according to claim 3, wherein the cage is firmly bonded to the first point and the second point by soldering, and wherein the cage is force-fitted to the third point and the fourth point by clamping.

5. The medical fluid pump according to claim 1, wherein the communication circuit board is connected to a plurality of antennas.

6. The medical fluid pump according to claim 5, wherein the plurality of antennas are arranged orthogonally to each other.

7. The medical fluid pump according to claim 5, wherein the plurality of antennas are connected to the communication circuit board via cables, each cable having a cable length, wherein the cable lengths are identical.

8. The medical fluid pump according to claim 5, wherein the plurality of antennas are spaced from each other by a distance corresponding to a multiple of a quarter wavelength of a transmission frequency of the plurality of antennas.

9. The medical fluid pump according to claim 1, wherein the communication circuit board is thermally coupled to the printed circuit board.

10. A medical fluid pump comprising:

a motor;

a printed circuit board having a control device of the motor; and a wireless communication module comprising a communication circuit board, the communication circuit board being arranged substantially perpendicular to the printed circuit board, wherein:

the communication circuit board is enclosed by a cage that is metallic or contains metallic elements, the cage is firmly bonded to the communication circuit board at a first point and a second point, and the cage is force-fitted to the communication circuit board at a third point and a fourth point.

11. The medical fluid pump according to claim 10, wherein the cage is firmly bonded to the first point and the second point by soldering, and wherein the cage is force-fitted to the third point and the fourth point by clamping.

12. A medical fluid pump comprising:

a motor;

a printed circuit board having a control device of the motor; and a wireless communication module comprising a communication circuit board, the communication circuit board being arranged substantially perpendicular to the printed circuit board, wherein:

the communication circuit board is connected to a plurality of antennas, and the plurality of antennas are arranged orthogonally to each other.

13. The medical fluid pump according to claim 12, wherein the plurality of antennas are connected to the communication circuit board via cables, each cable having a cable length, wherein the cable lengths are identical.

14. The medical fluid pump according to claim 12, wherein the plurality of antennas are spaced from each other by a distance corresponding to a multiple of a quarter wavelength of a transmission frequency of the plurality of antennas.

* * * * *